US00PP17870P2

(12) United States Plant Patent
Covington

(10) Patent No.: US PP17,870 P2
(45) Date of Patent: Jul. 17, 2007

(54) ***LANTANA* PLANT NAMED 'PRAISE HYMN'**

(50) Latin Name: *Lantana camara*
Varietal Denomination: Praise Hymn

(76) Inventor: Jim Covington, 214 West Lakeview Dr., Clinton, MS (US) 39056

( * ) Notice: Subject to any disclaimer, the term of this patent is extended or adjusted under 35 U.S.C. 154(b) by 8 days.

(21) Appl. No.: 11/269,181

(22) Filed: Nov. 8, 2005

(51) Int. Cl.
*A01H 5/00* (2006.01)

(52) U.S. Cl. ..... Plt./227
(58) Field of Classification Search ..... Plt./227
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Lantana* plant named 'Praise Hymn', characterized by its mounded and outwardly spreading plant habit; freely branching growth habit; freely flowering habit; flowers initially golden yellow in color becoming purple with development; and excellent garden performance.

1 Drawing Sheet

Botanical designation: *Lantana camara.*
Cultivar denomination: 'Praise Hymn'.

BACKGROUND OF THE INVENTION

The present Invention relates to a new and distinct cultivar of *Lantana* plant, botanically known as *Lantana camara,* and hereinafter referred to by the cultivar name Praise Hymn.

The new *Lantana* originated from an open-pollination of the *Lantana camara* cultivar Irene, not patented, as the female, or seed, parent with an unidentified selection of *Lantana camara,* not patented, as the male, or pollen, parent. The cultivar Praise Hymn was discovered and selected by the Inventor as a single plant within the progeny of the stated open-pollination in a controlled environment in Clinton, Miss. in June, 2000.

Asexual reproduction of the new cultivar by terminal cuttings in Clinton, Miss., since the fall of 2000, has shown that the unique features of this new *Lantana* are stable and reproduced true to type in successive generations.

SUMMARY OF THE INVENTION

Plants of the cultivar Praise Hymn have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Praise Hymn'. These characteristics in combination distinguish 'Praise Hymn' as a new and distinct cultivar:

1. Mounded and outwardly spreading plant habit.
2. Freely branching growth habit.
3. Freely flowering habit.
4. Flowers initially golden yellow in color becoming purple with development.
5. Excellent garden performance.

Plants of the new *Lantana* differ from plants of the female parent, the cultivar Irene, primarily in flower color as mature flowers of plants of the cultivar Irene are maroon in color.

Plants of the new *Lantana* can be compared to plants of the cultivar Balandroglo, disclosed in U.S. Plant Pat. No. 15,246. However, in side-by-side comparisons conducted by the Inventor in Clinton, Miss., plants of the new *Lantana* differed from plants of the cultivar Balandroglo in the following characteristics:

1. Plants of the new *Lantana* were more spreading and more vigorous than plants of the cultivar Balandroglo.
2. Plants of the new *Lantana* had thicker and stronger lateral branches than plants of the cultivar Balandroglo.
3. Plants of the new *Lantana* had golden yellow-colored flowers that with development became purple in color whereas plants of the cultivar Balandroglo had pale yellow-colored flowers that with development became dark pink in color.
4. Plants of the new *Lantana* and the cultivar Balandroglo differed in petal shape.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Lantana.*

The photograph at the top of the sheet comprises a side perspective view of a typical six-month old flowering plant of 'Praise Hymn' grown in a container.

The photograph at the bottom of the sheet comprises a close-up view of typical flowers and leaves of 'Praise Hymn'.

DETAILED BOTANICAL DESCRIPTION

In the following description, color references are made to The Royal Horticultural Society Colour Chart, 1995 Edition, except where general terms of ordinary dictionary significance are used. Plants were grown in 10-cm containers and under outdoor conditions in Clinton, Miss. during the summer. Plants were about three months old when the description was taken.

Botanical classification: *Lantana camara* cultivar Praise Hymn.

Parentage:

*Female, or seed, parent.*—*Lantana camara* cultivar Irene, not patented.

*Male, or pollen, parent.*—Unidentified selection of *Lantana camara,* not patented.

Propagation:

*Type cutting.*—Terminal cuttings.

*Time to initiate roots, summer.*—About 10 days at 38° C.

*Time to initiate roots, winter.*—About 15 days at 21° C.

*Time to develop roots, summer.*—About 25 days at 38° C.

*Time to develop roots, winter.*—About 70 days at 21° C.

*Root description.*—Numerous, fibrous and well-branched.

Plant description:

*Form.*—Perennial flowering plant; subshrub; initially upright, then outwardly spreading, mounded. Freely branching; lateral branches potentially forming at every node; pinching enhances lateral branch development.

*Plant height.*—About 24 cm.

*Plant diameter.*—About 22 cm.

*Vigor.*—Moderately vigorous.

*Lateral branches.*—Length: About 13 cm. Diameter: About 3.5 mm. Internode length: About 3.75 cm. Aspect: Initially upright, then bending about 45° from upright. Strength: Flexible, but strong. Texture: Pubescent; coarse. Color, young: Close to 144A. Color, woody: Close to 199A.

*Foliage description.*—Arrangement: Opposite, simple. Length: About 5.6 cm. Width: About 4.1 cm. Shape: Ovate. Apex: Acute. Base: Truncate. Margin: Serrate. Texture: Rough, coarse; pubescence on both surfaces; rugose. Fragrance: Pungent, herb-like. Color: Developing and fully expanded foliage, upper surface: Close to 147A. Developing and fully expanded foliage, lower surface: Close to 147B. Venation, upper surface: Close to 147B. Venation, lower surface: Close to 145D. Petiole length: About 1.4 cm. Petiole diameter: About 3 mm. Petiole color: Close to 145D.

Flower description:

*Flower type and habit.*—Small salverform flowers arranged in axillary umbels; flowers face mostly upward or outward. Flowers self-cleaning. Very freely flowering with potentially two inflorescences per node; typically about 25 flowers per umbel.

*Natural flowering season.*—Spring until frost in the autumn; flowering continuous.

*Flower longevity on the plant.*—About one week.

*Fragrance.*—Faint, sweet, pleasant.

*Inflorescence diameter.*—About 3.4 cm.

*Inflorescence height.*—About 1.8 cm.

*Flowers.*—Appearance: Flared trumpet, corolla fused, four-parted; flowers roughly rectangular in shape. Diameter: About 1.1 cm by 1 cm. Corolla tube length: About 1.3 cm.

*Flower buds* (*just before showing color*).—Length: About 3 mm. Diameter: About 2 mm. Shape: Oblong. Color: Close to 146A to 146B.

*Petals.*—Arrangement/appearance: Single whorl of four petals, fused into flared trumpet. Length from throat: Upper petal, about 5 mm; lower and lateral petals, about 4 mm. Width: Upper petal and lower petal, about 6 mm; lateral petals, about 4 mm. Shape: Upper and lower petals, somewhat spatulate; lateral petals, mostly orbicular. Apex: Mostly rounded. Base: Fused. Margin: Entire. Texture, upper and lower surfaces: Smooth, glabrous; satiny. Color: When opening, upper surface: Close to 9A to 12A. When opening, lower surface: Close to 10A. Fully opened, upper surface: Close to 78A. Fully opened, lower surface: Close to 155D underlain with close to 78A. Throat: Close to 155D. Tube: Close to 155D underlain with close to 78A.

*Sepals.*—Arrangement/appearance: One per flower at the base of the corolla; leaf-like. Length: About 5 mm. Width: About 1.75 mm. Shape: Linear. Apex: Sharply acute. Margin: Entire. Texture: Pubescent. Color, upper and lower surfaces: Close to 144A.

*Peduncles.*—Length: About 2 cm. Diameter: About 2 mm. Angle: About 30° to 45° from the stem. Strength: Flexible, but strong. Color: 144A.

*Pedicels.*—Length: Less than 1 mm. Diameter: Less than 1 mm. Color: Close to 144A.

*Reproductive organs.*—Stamens: Quantity: About four. Anther shape: Oblong. Anther length: Less than 1 mm. Anther color: Close to 9A. Pollen amount: None observed. Pistils: Quantity: One. Pistil length: Less than 1 mm. Stigma color: Close to 144A. Style color: 144D. Ovary color: 144A.

*Fruit/seed.*—Fruit and seed production has not been observed.

Disease/pest resistance: Plants of the new *Lantana* have not been noted to be resistant to pathogens and pests common to *Lantana.*

Weather tolerance: Plants of the new *Lantana* have been observed to be tolerant to rain, wind and to temperatures above 43° C., and hardy to about USDA Hardiness Zone 8.

It is claimed:

1. A new and distinct cultivar of *Lantana* plant named 'Praise Hymn', as illustrated and described.

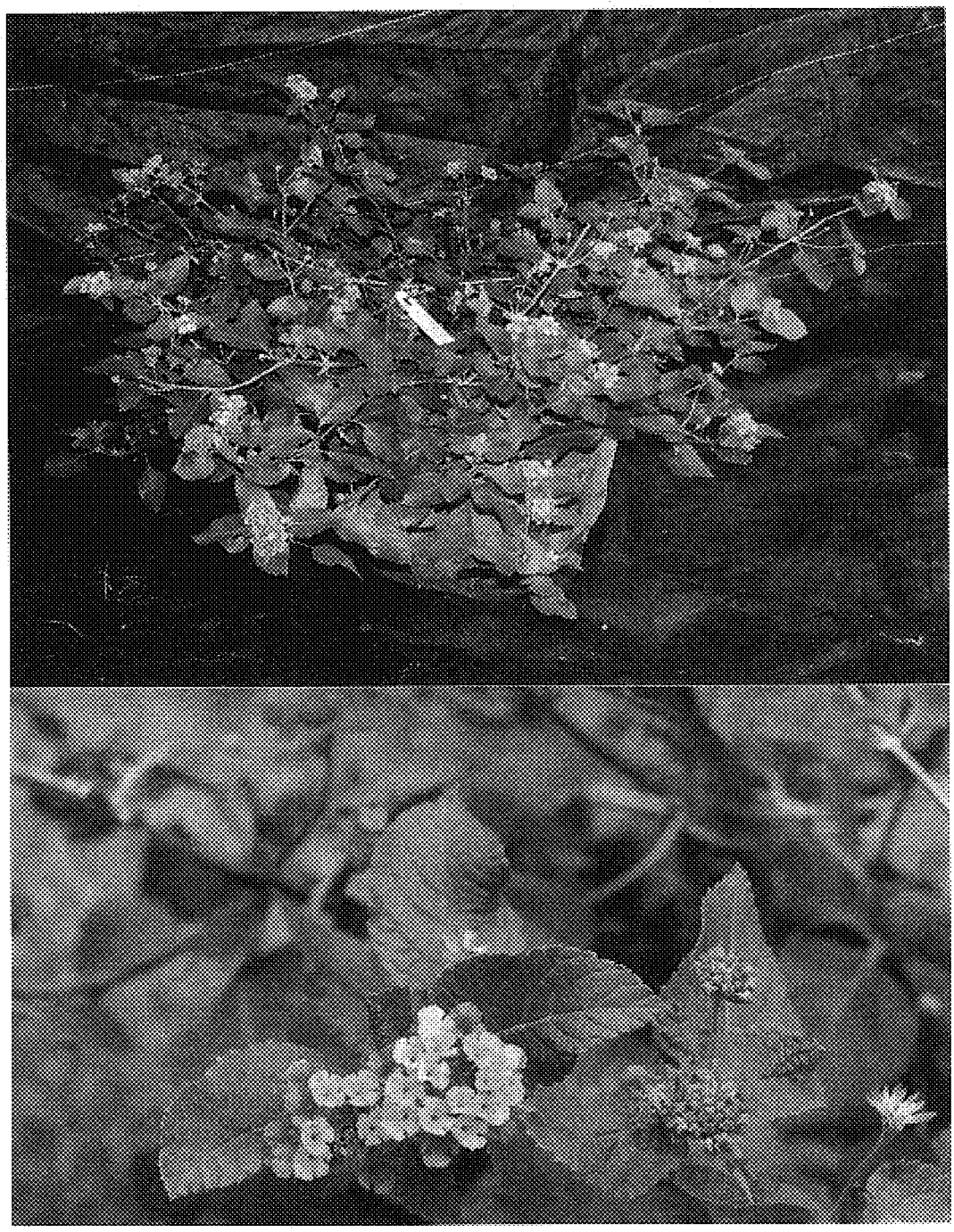

* * * * *